United States Patent [19]

Kitamura et al.

[11] Patent Number: 5,469,752
[45] Date of Patent: Nov. 28, 1995

[54] APPARATUS FOR AUTOMATICALLY INSPECTING POWDERY PRODUCTS FOR THE PRESENCE OF FOREIGN SUBSTANCES

[75] Inventors: Hajime Kitamura, Ichihara; Masaru Takeuchi; Hideo Yoshikoshi, both of Hasaki; Mikio Kitai, Mito; Takashi Chino, Iruma; Yuji Nogami, Kawaguchi; Hajime Yashiro, Sagara; Keisuke Kato, Kawasaki, all of Japan

[73] Assignee: Shin-Etsu Chemical Co., Ltd., Japan

[21] Appl. No.: 167,029

[22] Filed: Dec. 16, 1993

[30] Foreign Application Priority Data

Dec. 28, 1992 [JP] Japan .................. 4-349561

[51] Int. Cl.$^6$ ................. G01N 21/29; G01N 33/44
[52] U.S. Cl. ................. 73/866; 73/865.8
[58] Field of Search .................. 73/866, 865.8, 73/865.5, 864.81, 863.86, 863.21; 198/339.1; 204/580–582, 939; 241/16, 38, 46.11, 101.3, 101.8; 348/125, 127, 128; 358/106, 107; 356/38, 237

[56] References Cited

U.S. PATENT DOCUMENTS

| | | | |
|---|---|---|---|
| 2,353,828 | 7/1944 | Hyde | 73/863.21 |
| 4,615,902 | 10/1986 | Falcoff et al. | 209/581 |
| 4,821,782 | 4/1989 | Hyer | 141/83 |
| 4,842,761 | 6/1989 | Rutherford | 252/90 |
| 4,887,475 | 12/1989 | Austin et al. | 73/866 |
| 4,976,540 | 12/1990 | Kitamura et al. | 356/38 |
| 5,074,158 | 12/1991 | Tokoyama | 73/865.8 |
| 5,130,092 | 7/1992 | Liu | 241/16 |
| 5,157,976 | 10/1992 | Tokoyama et al. | 73/865.8 |
| 5,259,749 | 11/1993 | Meixner et al. | 425/205 |
| 5,261,285 | 11/1993 | Tokoyama | 73/865.8 |

FOREIGN PATENT DOCUMENTS

| | | | |
|---|---|---|---|
| 541042 | 5/1957 | Canada | 241/101.8 |
| 2632879 | 12/1989 | France | 209/582 |
| 698108 | 11/1940 | Germany | 241/46.11 |
| 1207302 | 12/1965 | Germany | 209/581 |
| 1507514 | 4/1969 | Germany | 241/16 |
| 3105558 | 9/1982 | Germany | 241/101.8 |
| 3443476 | 5/1986 | Germany | 209/581 |
| 5588 | 2/1981 | Japan | 241/16 |
| 58810 | 4/1985 | Japan | 241/101.8 |
| 43743 | 2/1989 | Japan | 73/865.5 |
| 8304371 | 7/1985 | Netherlands | 358/106 |
| 634177 | 11/1978 | U.S.S.R. | 73/866 |
| 1516311 | 10/1989 | U.S.S.R. | 73/866 |
| 1279695 | 6/1972 | United Kingdom | 241/16 |

*Primary Examiner*—Hezron E. Williams
*Assistant Examiner*—Daniel S. Larkin
*Attorney, Agent, or Firm*—Parkhurst, Wendel & Rossi

[57] ABSTRACT

An apparatus for automatically and continuously inspecting a powdery product for the presence of foreign substances as contaminants, which permits highly precise inspection of powdery products, comprises static charge eliminator 10 for eliminating electrostatic charges generated on a powdery sample supplied to the apparatus; hopper 41 for receiving and storing the powdery sample whose electrostatic charges have been eliminated and dropped onto the hopper through static charge eliminator 10; conveyor 42 for conveying the powdery sample, as a subject to be photographed, discharged from hopper 41 and spread over conveyor 42 in the form of a layer having a uniform thickness; and video camera 43 for photographing, over a predetermined visual field, the powdery sample on the subject-conveyor. Images taken by video camera 43 do not include those originated from dark spots due to unevenness of the powdery sample distribution, but includes only those originated from foreign substances even when inspecting a powdery sample which is liable to be electrically charged such as a vinyl chloride resin, since the powdery sample is not agglomerated.

7 Claims, 5 Drawing Sheets

APPARATUS FOR AUTOMATICALLY INSPECTING POWDERY PRODUCTS FOR THE PRESENCE OF FOREIGN SUBSTANCES

BACKGROUND OF THE INVENTION

The present invention relates to an apparatus for automatically examining and inspecting white resin powder of, for instance, vinyl chloride resins, ABS resins and MBS resins for the presence of foreign substances.

When preparing resin powder or forwarding the powdery product from a manufacturing plant, the product is in general subjected to quality inspection for various predetermined properties. The results are sent back to the manufacturing plant for the improvement of production processes or they are used in the denoration of the quality in order to afford convenience to the destination or the consignee.

In case of, for instance, vinyl chloride resin powder, one of the items for quality inspection thereof is to inspect the resin powder for the presence of foreign substances as contaminants. Conventionally, the inspection of the powdery resin product for the presence of foreign substances has been carried out by spreading a constant amount of the vinyl chloride resin powder and searching for the presence of pigmented foreign substances (such as those colored black, brown and/or red) thus to count the number of foreign substances present therein. However, the results widely vary depending on the visual power and the nature of each inspector. Accordingly, this method never provides objectively measured values, requires much labor and time and accordingly, has low efficiency.

Incidentally, there has recently been used an industrial apparatus for automatic visual inspection which makes use of a video camera. An example of such apparatuses is one which is commercially available from Hajime Sangyo Co., Ltd. under the trade name of FF 4000. This apparatus serves to detect, for instance, defects, stains and foreign substances on the image of a powdery resin sample photographed by the video camera and to specify the positions of the foreign substances on the photograph through blinking modulated bright spots on a monitor. This inspection apparatus permits automatic inspection of a subject for the presence of, for instance, foreign substances and can provide measured values free of any scattering irrespective of inspectors. Moreover, the apparatus does not require much labor and time and ensures efficient inspection.

However, when the aforementioned industrial apparatus for automatic visual inspection which makes use of a video camera is used in the inspection of resin powder easily electrostatically charged such as vinyl chloride resin powder for the presence of colored foreign substances as contaminants thereof, it is often observed that the resin powder to be inspected is not uniformly dropped on a belt conveyor or is unevenly distributed on the belt conveyor due to electrostatic charges generated on the resin powder per se. For this reason, the surface of the spread resin powder layer becomes severely uneven and this leads to a large scattering in the measured values. Consequently, the apparatus does not provide any reproducible result.

SUMMARY OF THE INVENTION

Accordingly, the present invention has been developed for solving the foregoing problems associated with the conventional techniques for the inspection of powdery resin products for the presence of foreign substances. An object of the present invention is thus to provide an apparatus for automatically inspecting a powdery product for the presence of foreign substances present therein as contaminants, wherein the conventional industrial device for automatic visual inspection is improved in such a manner that the device is adapted to the inspection of powdery products for the presence of foreign substances and which permits highly precise detection and/or determination of foreign substances present in the powdery products without requiring much labor.

Figure 1A:
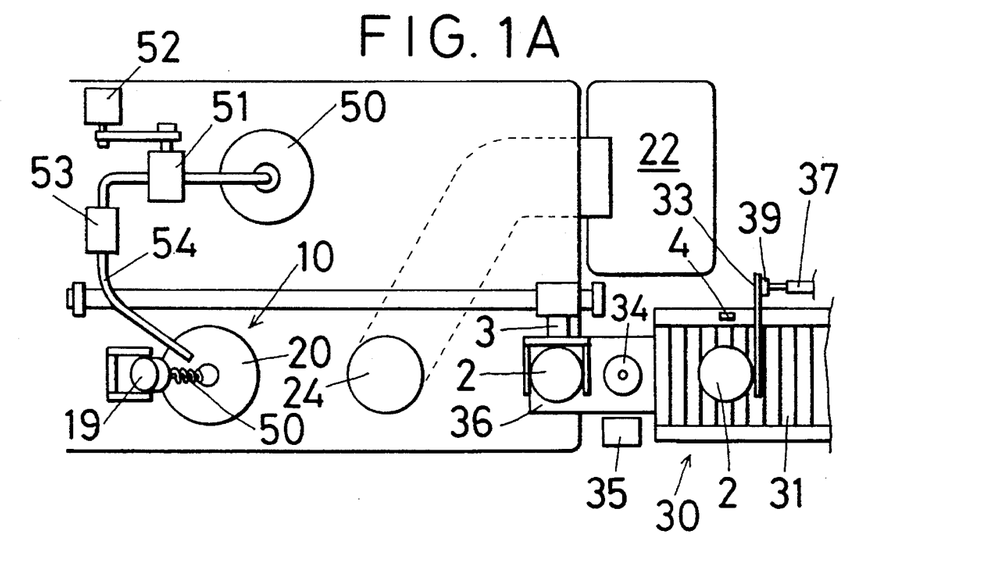
FIG. 1A is a top plan view illustrating an embodiment of the apparatus for automatically inspecting a powdery product for the presence of foreign substances according to the present invention.
Figure 1B:
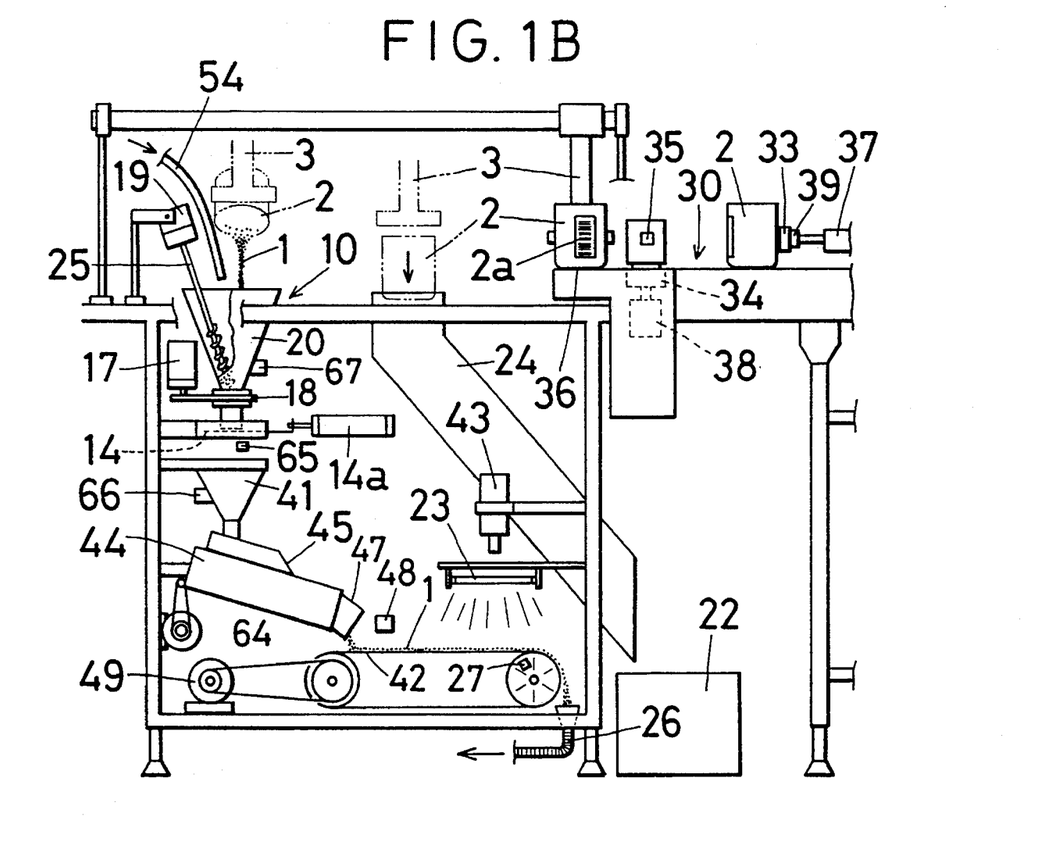
FIG. 1B is an elevational view of the embodiment illustrated in FIG. 1A.

The apparatus for automatically inspecting a powdery product for the presence of foreign substances according to the present invention comprises, as shown in FIGS. 1A and 1B, static charge eliminator 10 for eliminating electrostatic charges on powdery sample 1 supplied to the apparatus; hopper 41 for receiving and storing powdery sample 1 which has been electrically neutralized and dropped thereto through static charge eliminator 10; conveyor 42 for conveying the powdery sample, as a subject to be photographed, discharged from hopper 41 and spread over the conveyor in the form of a layer having a uniform thickness; and video camera 43 for photographing, over a predetermined visual field thereof, powdery sample 1 on conveyor 42 for conveying the subject to be photographed.

The apparatus is further provided with robot 3 which holds and conveys sample container 2 accommodating powdery sample 1 and which supplies powdery sample 1 to static charge eliminator 10. Robot 3, static charge eliminator 10, conveyor 42 for conveying the subject, and video camera 43 are operated under the regulation of control circuits 61 and 62 (see FIG. 3). Preferably, the apparatus is further provided with conveying device 30 for conveying sample container 2 accommodating powdery sample 1 to the position at which robot 3 holds sample container 2.

Figure 2:
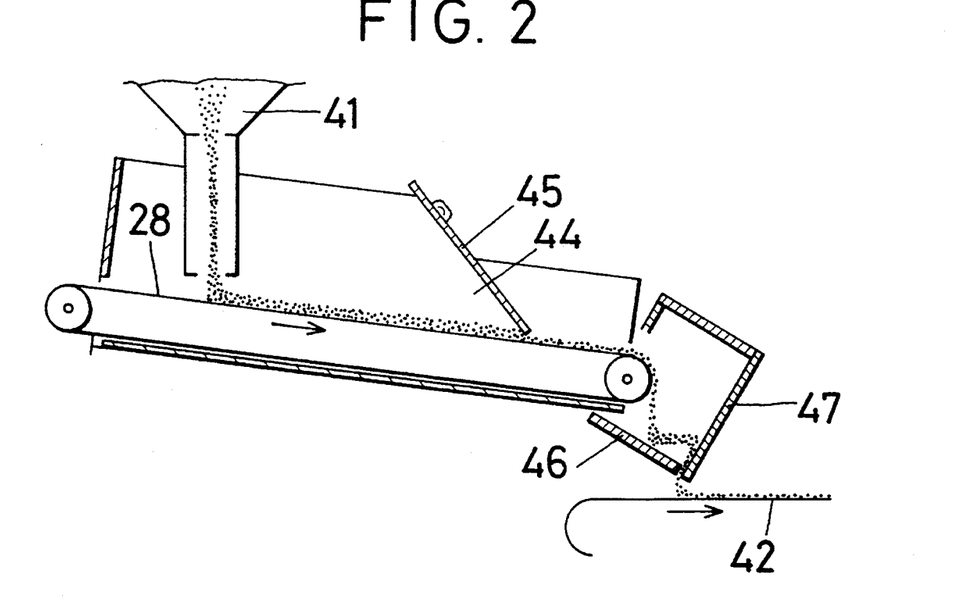
FIG. 2 is an enlarged perspective view illustrating the principal part of the apparatus shown in FIG. 1B.

A specific example of the device for spreading powdery sample 1 on the conveyor in the form of a layer having a uniform thickness is one shown in FIG. 2 which comprises belt conveyor 28 for conveying the powdery sample discharged from hopper 41; leveling plate 45 which is brought into contact with the upper portion of the powdery sample positioned on the conveying path and transported by conveyor 28 thus to spread uniformly the sample over the conveying path of conveyor 28; and buffer plates 46 and 47 which are positioned at the end of belt conveyor 28 and receive the powdery sample dropped thereto through belt conveyor 28. The powdery sample reflected by buffer plates 46 and 47 is dropped onto conveyor 42 for conveying the subject to be photographed. Belt conveyor 28 is also operated under the regulation of the control circuits.

Bar code 2a on which the lot number of the sample and/or conditions for inspection are recorded is attached to sample container 2 accommodating powdery sample 1. The apparatus is thus provided with bar code reader 35 for reading the data recorded on bar code 2a and control circuits 61 and 62 preferably regulate the operations of static charge eliminator 10 and video camera 43 on the basis of the sample lot number and/or the conditions for inspection read by bar code reader 35.

Figure 3:
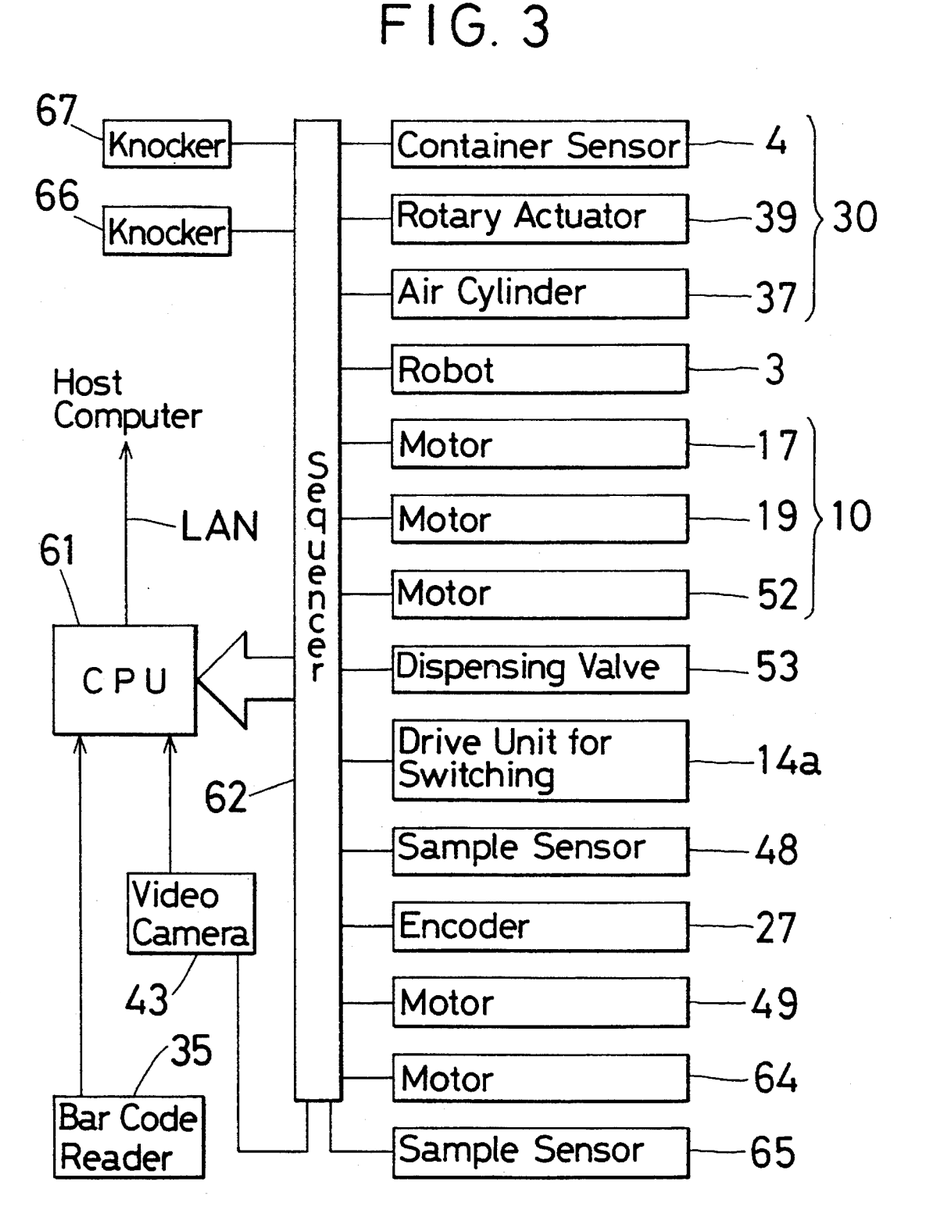
FIG. 3 is a block diagram illustrating the control system of the apparatus for automatically inspecting a powdery product for the presence of foreign substances according to the present invention.

Control circuit 61 is connected to a host computer as shown in FIG. 3 so that control circuit 61 can transfer the data of foreign substances photographed by video camera 43 to the host computer together with the sample lot number of the powdery sample 1 and/or the conditions for inspection.

Static charge eliminator 10 specifically comprises funnel 20 equipped with shutter 14, screw-agitator 25 inserted therein and tube 54 which is introduced into funnel 20 and connected to supply source 50 for static charge-elimination liquid. Funnel 20 is connected to rotary drive unit 17. In this respect, it is preferred that screw-agitator 25 has a rotation axis approximately parallel to the inclined inner wall of funnel 20 and that the direction of rotation of funnel 20 is opposite to that of screw-agitator 25.

The foregoing apparatus for automatically inspecting a powdery product for the presence of foreign substances according to the present invention can suitably be used for inspecting vinyl chloride resin powder, which is liable to be electrically charged, for the presence of foreign substances.

DETAILED EXPLANATION OF THE INVENTION

In the apparatus for automatically inspecting a powdery product for the presence of foreign substances according to the present invention, powdery sample 1 is discharged from static charge eliminator 10, dropped onto the surface of conveyor 42 for conveying a subject to be photographed and spread thereon in the form of a layer having a uniform thickness. The powdery sample can be inspected for the presence of foreign substances on the basis of a photograph taken by video camera 43. As has been discussed above, the electrostatic charges generated on powdery sample 1 are neutralized or eliminated by static charge eliminator 10 and accordingly, the powdery sample can evenly be spread over conveyor 42 for conveying a subject to be photographed in the form of a layer having a uniform thickness. For this reason, any dark spots due to unevenness of the powdery sample spread on the conveyor are not present on the photographs taken by the video camera and therefore, only the dark spots due to the presence of foreign substances remain on the photograph as images. Thus, reproducible measured values can be obtained since any scatter in the resulting data on the foreign substances is not observed.

The apparatus according to the present invention will hereunder be explained in more detail with reference to specific embodiments while referring to the accompanying drawings, but the present invention is by no means limited to these specific embodiments.

FIG. 1A is a top plan view of the apparatus for automatically inspecting a powdery product for the presence of foreign substances according to the present invention and FIG. 1B is an elevational view of the apparatus shown in FIG. 1A.

As seen from FIGS. 1A and 1B, device 30 for conveying sample container 2 comprises roller conveyor 31, bar code reader 35 and conveyor table 36 which are arranged in this order. Sample container 2 accommodates powdery resin sample 1 in a predetermined amount required for the inspection and bar code 2a which carries coded conditions for inspection such as the name of the sample, the sample lot number and items for inspection is attached onto the outer surface of sample container 2.

Container sensor 4 is positioned on the side face of roller conveyor 31 and air cylinder 37 which moves back and forth is arranged in parallel relation with respect to the conveying path of roller conveyor 31. Conveying bar 33 is fitted to the tip of the movable part of air cylinder 37 through rotary actuator 39. Conveying bar 33 not only can perform reciprocating motion between the position above roller conveyor 31 and the position above conveyor table 36 in response to the reciprocating movement of air cylinder 37, but also can perform vibrational motion in such a manner that it goes across the conveying path on roller conveyor 31 in response to the operation of rotary actuator 39.

Bar code reader 35 is fitted to one side of turn table 34 positioned at the end of roller conveyor 31. Turn table 34 is a disk-like table connected to gear motor 38. A flat plane adjacent to turn table 34 serves as conveyor table 36 for transferring sample container 2, whose bar code has been read, to the subsequent step.

Static charge eliminator 10 comprises funnel 20 and screw-agitator 25 inserted in funnel 20. The external wall of funnel 20 is rotatably supported by an axis and connected to motor 17 as a rotary drive unit through belt 18. Screw-agitator 25 is provided with driving motor 19. The rotation axis of screw-agitator 25 is arranged in an approximately parallel relation with respect to the inclined inner wall of funnel 20, and funnel 20 is rotated in response to the operation of motor 17 in the direction opposite to the rotational direction of screw-agitator 25. Shutter 14 is closely fitted to the outside of an exhaust port of funnel 20. Shutter 14 is connected to drive unit 14a for electromagnetically controlling shutter 14. Moreover, the tip of tube 54 for supplying a liquid for eliminating electrostatic charges is inwardly introduced into funnel 20. Tube 54 for supplying a liquid for eliminating electrostatic charges is, in order, connected to electromagnetically dispensing valve 53, feed pump 51 and tank 50 for storing the static charge-elimination liquid. Feed pump 51 is connected to motor 52. Electromagnetically operating-knocker 67 is fitted to the outside of funnel 20 to tap the outer wall thereof thus to facilitate the dropping of the powdery sample.

Hopper 41 is arranged below static charge eliminator 10. Electromagnetically operating-knocker 66 is fitted to the outside of hopper 41 to tap the outer wall of the hopper for the purpose of facilitating the dropping of the powdery sample. Moreover, belt conveyor 28 connected to motor 64 as a drive unit is positioned, below hopper 41, in such a manner that it is inclined towards the forward direction, as shown in FIG. 2. Leveling plate 45 is arranged over belt conveyor 28 while leaving a slight gap between belt conveyor 28 and the tip of leveling plate 45. In this respect, leveling plate 45 is secured onto side plate 44 through a long hole by tightening screws so that the size of the gap can be adjusted. Buffer plates 46 and 47 are positioned at the end of belt conveyor 28 and receive and reflect the powdery sample dropped thereto through belt conveyor 28 thus to prevent scattering of the powdery sample. Sample sensor 48 is positioned in close proximity to the exhaust port of buffer plate 47. In addition, sample sensor 65 is arranged above hopper 41 and can see the surface of belt conveyor 28 through the hopper.

Furthermore, conveyor 42 for conveying a subject to be photographed which is connected to motor 49 as a drive unit is arranged below leveling plate 47. Encoder 27 is fitted to conveyor 42 for conveying a subject to be photographed. Video camera 43 is positioned above the front portion of conveyor 42 for conveying the subject. Xenon lamp 23 is likewise positioned above conveyor 42 and below video camera 43 so as to illuminate the region on conveyor 42 corresponding to the visual field of video camera 43. The surface of conveyor 42 for conveying the subject is colored white so that foreign substances (mainly colored black) possibly present in the powdery sample (white) can be observed, as dark spots, on the photograph taken by video camera 43. Hose 26 is positioned below the end portion of conveyor belt 42 for conveying the subject and the end of the hose is connected to a suction device (not shown) so that it receives the powdery sample which has been already inspected and abandons the sample.

As will be seen from FIG. 3, in the foregoing apparatus, sequencer 62 is connected to container sensor 4 fitted to conveying device 30, air cylinder 37, rotary actuator 39, robot 3, driving motor 17 for rotating funnel 20, driving motor 19 for rotating screw-agitator 25, driving motor 52 for the operation of feed pump 51, electromagnetically dispensing-valve 53, drive unit 14a for switching shutter 14, sample sensor 48, encoder 27, motors 49 and 64, knockers 66 and 67, sample sensor 65 and video camera 43 and sequencer 62 is, in turn, connected to arithmetic and control unit 61 (central processing unit: CPU). Moreover, bar code reader 35 and video camera 43 are also connected to arithmetic and control unit 61 and the latter is connected to the host computer through a local area network (LAN).

The apparatus for automatically inspecting a powdery product for the presence of foreign substances according to the present invention is in general operated as follows. The overall control of the apparatus is performed in accordance with the program incorporated into arithmetic and control unit 61 (CPU), while the function of each device is controlled according to the control program incorporated into sequencer 62. The function of the apparatus will hereunder be detailed in the light of the program chart incorporated into arithmetic and control unit 61 shown in FIG. 4 and the control program chart incorporated into sequencer 62 depicted as a subroutine A (see FIG. 5) and subroutine B (see FIG. 6) for the program chart of CPU.

An amount ranging from 300 to 1200 cc of powdery sample 1 is weighed out and introduced into sample container 2. A label carrying bar code 2a is attached to the side face of sample container 2, bar code 2a carrying coded data concerning the production lot number, the inspection number of the sample and the conditions for inspection of the sample. Sample container 2 is placed on roller conveyor 31 and transferred to a desired position.

Figure 4:
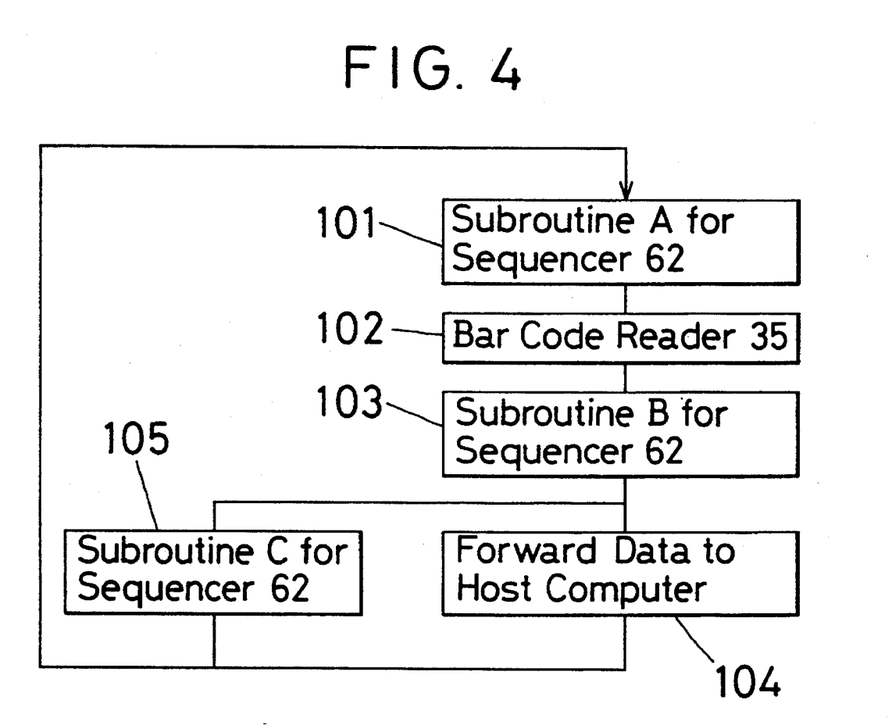
FIG. 4 is a program chart for an arithmetic and control unit used in the apparatus of the present invention.
Figure 5:
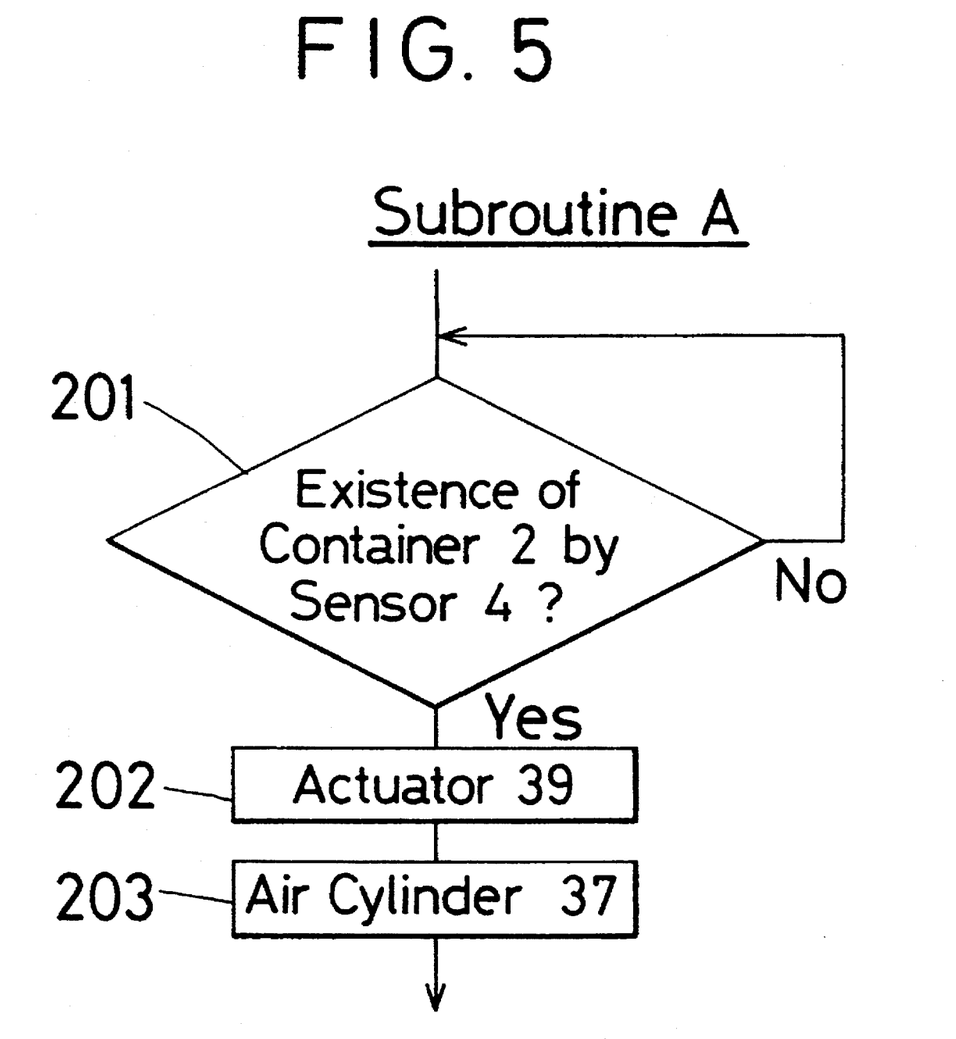
FIG. 5 is a control program chart for a sequencer used in the apparatus of the present invention.

After confirming whether the apparatus is in its reset state or not, sample container 2 is put on turn table 34 by the action of conveying device 30 operated according to the instruction outputted from arithmetic and control unit 61 which is inputted to device 30 through the subroutine A (shown in FIG. 5) for sequencer 62 in the step 101 shown in FIG. 4. After container sensor 4 detects or confirms the presence of sample container 2 (step 201), rotary actuator 39 is started (step 202) and correspondingly conveying bar 33, which has been stood upright at an upper position, is rotated and shifted in such a manner that it is positioned just behind sample container 2. Then air cylinder 37 is put in operation (step 203) so that conveying bar 33 pushes sample container 2 towards turn table 34 and transfers sample container 2 to turn table 34. After the completion of this operation, air cylinder 37 temporarily restores to its original position, then rotary actuator 39 is put in restoration operation and conveying bar 33 rotates and upwardly moves in response to the operation of actuator 39. In other words, these means restore their home positions.

After sample container 2 is put on turn table 34, bar code reader 35 reads bar code 2a by the instruction outputted from arithmetic and control unit 61 in the step 102. Bar code reader 35 can scan over bar code 2a to read it while rotating sample container 2 on turn table 34 by the operation of motor 38. Bar code reader 35 then decodes the coded data concerning the production lot number, the inspection number and the conditions for inspection of the powdery sample and forwards these data to arithmetic and control unit 61.

In the step 103, robot 3 conveys sample container 2 and substitutes a new powdery sample for powdery sample 1, which has already been inspected, by the instruction outputted from arithmetic and control unit 61 which is inputted to robot 3 through the subroutine B (shown in FIG. 6) for sequencer 62. In the step 301, robot 3 holds and lifts up sample container 2 placed on turn table 34 and is put in turning operation to convey sample container 2 towards a position situated above funnel 20. When sample container 2 is turned upside down by the rotation of the tip of the arm as indicated in phantom lines in FIG. 1B, the powdery sample 1 is dropped to funnel 20 and stored therein.

If motor 17 is put in operation at this stage (step 302), funnel 20 correspondingly rotates in response to the rotation of motor 17. Moreover, screw-agitator 25 starts agitation of powdery sample 1 present in funnel 20 in response to the rotational motion of motor 19 (step 303). If motor 52 is rotated (step 304), feed pump 51 is put in operation and in turn pumps up a static charge-elimination liquid accommodated in tank 50. If electromagnetic dispensing valve 53 is simultaneously put in operation at this stage (step 305), a predetermined amount of the static charge-eliminating liquid passes through tube 54 and is poured on agitated powdery sample 1. After properly stirring and mixing them, motors 17 and 19 are interrupted. In this respect, funnel 20 is preferably rotated in the rotational direction opposite to that of screw-agitator 25 in order to enhance the mixing efficiency. The static charge-eliminating liquid usable herein may be, for instance, a solution of a cationic surfactant in a solvent such as isopropyl alcohol. The use of such a volatile solvent such as isopropyl alcohol allows rapid and efficient evaporation thereof from powdery sample 1 and thus only the surfactant as an effective component remains on powdery sample 1.

At this stage, belt conveyor 28 starts rotation in response to the starting of motor 64 (step 306) and simultaneously conveyor 42 for conveying the subject to be photographed starts rotation in response to the starting of motor 49 (step 307). Then drive unit 14a for electromagnetic switching is started so as to open Shutter 14 (step 308), knocker 67 begins to operate to tap funnel 20 (step 309), knocker 66 also begins to operate to tap hopper 41 (step 310) and accordingly, powdery sample 1 drops onto belt conveyor 28. In this-respect, these steps 308 to 310 can be carried out without any trouble due to electrostatic charges on powdery sample 1 since the sample has already been destaticized as discussed above. As belt conveyor 28 has been put in operation, powdery sample 1 dropped thereon is downstream transferred. Powdery sample 1 on belt conveyor 28 is uniformly spread in the direction of the width thereof (or horizontal direction) by the action of leveling plate 45 in the course of the transportation of the powdery sample so that the amount of powdery sample 1 transferred per unit time (flow rate) is kept constant. In this respect, the flow rate of the powdery sample can be controlled by shifting the position in a long hole at which leveling plate 45 is secured through tightening screws through the hole. After powdery sample 1 passes through leveling plate 45, it is transferred in the form of a layer having a uniform thickness and drops from belt conveyor 28 at the end thereof. Buffer plate 46 receives and reflects powdery sample 1 dropped from conveyor 28 and then buffer plate 47 likewise reflects sample 1 thus to relax the shock upon dropping of the sample and to prevent any scatter of powdery sample 1. Buffer plates 46 and 47 thus ensure the dropping of powdery sample 1 onto conveyor 42 for the subject to be photographed as a layer having predetermined width and thickness.

Figure 6:
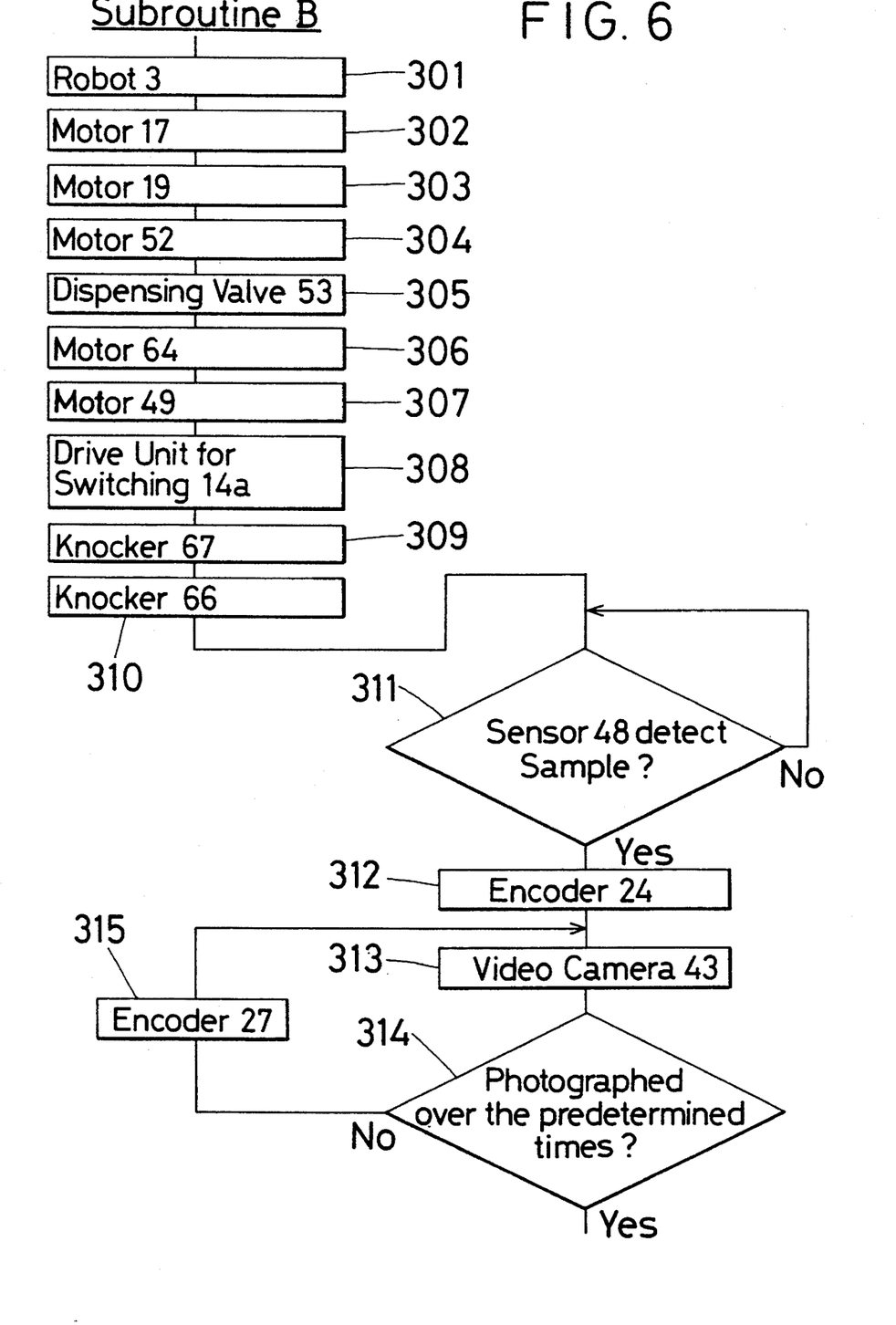
FIG. 6 is a control program chart for a sequencer used in the apparatus of the present invention.

As will be seen from the step 311 shown in FIG. 6, if sample sensor 48 confirms the presence of powdery sample 1 dropped on belt conveyor 42, encoder 27 performs pulse-count over a predetermined times, i.e., till the timing at which the visual field of video camera 43 sufficiently encompasses powdery sample 1 on belt conveyor 42 (step 312). At an instance at which the pulse-count operation has been completed, video camera 43 is put in operation to take photographs of powdery sample 1 (step 313). Any foreign substance possibly present in sample 1 appears as dark spots on the photographs taken by video camera 43 and then the image signals of the foreign substances are inputted to arithmetic and control unit 61. If powdery sample is not photographed over the predetermined times (step 314), encoder 27 first performs pulse-count over the predetermined times, i.e., till the timing at which powdery sample 1 on belt conveyor 42 moves to a visual field of video camera 43 different from the preceding one (step 315) and then video camera 43 is again put in operation to take predetermined number of photographs (step 313).

The resulting image signals are likewise inputted to arithmetic and control unit 61. These operations are repeated over predetermined times (for instance, 10 times) to complete photographing operations (step 314). Powdery sample 1 which has been photographed is successively transferred by belt conveyor 42, dropped into exhaust hose 26 and drawn in a suction device (not shown).

In step 104, the data concerning the production lot number, the inspection number and the conditions for inspection of the powdery sample inputted to arithmetic and control unit 61 in step 102 are forwarded to the host computer, through the LAN, together with the image signals likewise inputted to arithmetic and control unit 61. In this respect, these data can be outputted through a display device or a printer (not shown) connected to arithmetic and control unit 61.

In the foregoing step 103, i.e., the step 301 of the subroutine B, robot 3 rotates while holding sample container 2 accommodating powdery sample 1 to make container 2 empty, then robot 3 is put in operation according to the subroutine C for sequencer 62 (each step is not shown) in the step 105 to move the sample container to a position above exhaust chute 24 as shown by a chain line B depicted on FIG. 1 and to set sample container 2 free at this stage. Sample container 2 then passes through chute 24 and is received by and accommodated in exhaust box 22. After setting the container free, robot 3 is in the stand-by condition (or in its home position) on conveyor table 36.

After the completion of the foregoing series of the operation steps 101 to 105, the apparatus resets.

As has been explained above in detail, the apparatus for automatically inspecting a powdery product for the presence of foreign substances according to the present invention permits automatic and continuous inspection of the powdery product for the presence of foreign substances and is effective for the reduction of labor required for the inspection of powdery products. Moreover, the apparatus of the present invention permits the elimination of any scatter in the measured value depending on inspectors and/or due to various accidental factors and, therefore, can provide reproducible and accurate measured values from a statistical standpoint. Since the inspection is carried out after electrostatic charges on powdery samples are eliminated, the powdery sample is not agglomerated and is uniformly spread in the form of a layer. Thus, image signals do not include those originated from dark spots due to unevenness of the powdery sample distribution, but include only those originated from foreign substances, and this in turn permits reproducible and highly precise inspection of the powdery sample for the presence of foreign substances. In addition, the inspection apparatus according to the present invention is improved in such a manner that all of the factors which make the measured value inaccurate are eliminated and permits highly precise inspection in this respect as well.

What is claimed is:

1. An apparatus for automatically inspecting a powdery material for presence of foreign substances, comprising:

a static charge eliminator for eliminating electrostatic charges generated on a powdery sample supplied to the apparatus, said static charge eliminator comprising a funnel having a shutter, a first rotary drive unit means for rotating the funnel, a first knocker for tapping said funnel, an agitator for agitating the powdery sample in said funnel, said agitator comprising a screw-agitator which has a rotation axis approximately parallel to an inclined inner wall of the funnel and a second rotary drive unit means for rotating the screw-agitator in a direction opposite to a rotation direction of the funnel, and a source for supplying static-charge eliminator liquid to the powdery sample in said funnel;

a hopper for receiving and storing the powdery sample from said static charge eliminator, said hopper including a second knocker for tapping the hopper;

a conveyor for conveying the powdery sample from the hopper;

a spreader for spreading the powdery sample over the conveyor in the form of a layer having a uniform thickness; and a video camera for photographing, over a predetermined visual field, the powdery sample on the conveyor.

2. The apparatus according to claim 1, wherein said spreader comprises a belt conveyor for conveying the powdery sample from the hopper to the conveyor, a leveling plate which is positioned to level the powdery sample on the belt conveyor, and buffer plates which are positioned at an end of the belt conveyor to receive the powdery sample dropped thereto from the belt conveyor, wherein the powdery sample is reflected by the buffer plates and dropped onto the conveyor.

3. The apparatus according to claim 2, further comprising a robot for holding and conveying a sample container accommodating the powdery sample to supply the powdery sample to the static charge eliminator, and a control circuit for operating the robot, the static charge eliminator, the belt conveyor, the conveyor and the video camera.

4. The apparatus according to claim 3, further comprising a bar code reader for reading a bar code which is attached to the sample container, wherein said control circuit regulates operations of the static charge eliminator and the video camera based upon information read by the bar code reader.

5. The apparatus according to claim 4, further comprising a host computer to which the control circuit transfers information from the video camera and information read by the bar code reader.

6. The apparatus according to claim 3, further comprising a conveying device for conveying the sample container to a position at which the robot may hold the sample container.

7. The apparatus according to claim 1, wherein the powdery sample is a vinyl chloride resin.

* * * * *